(12) United States Patent
Sagmeister

(10) Patent No.: US 11,298,248 B2
(45) Date of Patent: Apr. 12, 2022

(54) ORTHOPEDIC DEVICE

(71) Applicant: Otto Bock Healthcare Products GmbH, Vienna (AT)

(72) Inventor: Luis Sagmeister, Pitten (AT)

(73) Assignee: Otto Bock Healthcare Products GmbH, Vienna (AT)

( * ) Notice: Subject to any disclaimer, the term of this patent is extended or adjusted under 35 U.S.C. 154(b) by 0 days.

(21) Appl. No.: 16/638,710

(22) PCT Filed: Jul. 30, 2018

(86) PCT No.: PCT/EP2018/070604
§ 371 (c)(1),
(2) Date: Feb. 12, 2020

(87) PCT Pub. No.: WO2019/048136
PCT Pub. Date: Mar. 14, 2019

(65) Prior Publication Data
US 2020/0360160 A1 Nov. 19, 2020

(30) Foreign Application Priority Data

Sep. 6, 2017 (DE) ...................... 10 2017 120 463.6

(51) Int. Cl.
*A61F 2/68* (2006.01)
*A61F 2/58* (2006.01)

(52) U.S. Cl.
CPC ................ *A61F 2/68* (2013.01); *A61F 2/586* (2013.01); *A61F 2002/6863* (2013.01)

(58) Field of Classification Search
CPC .... A61F 2/68; A61F 2/586; A61F 2002/6863; A61F 5/01; F16D 7/00
See application file for complete search history.

(56) References Cited

U.S. PATENT DOCUMENTS

| 3,240,304 A | 3/1966 | Wickersham |
| 4,651,856 A * | 3/1987 | Skrobisch ............... F16D 7/025 192/150 |
| 4,825,992 A * | 5/1989 | Skrobisch ................ F16D 7/00 192/56.4 |
| 9,066,817 B2 | 6/2015 | Gilbert et al. |
| 2015/0216679 A1 | 8/2015 | Lipsey et al. |
| 2016/0038314 A1 | 2/2016 | Kuiken et al. |
| 2016/0089251 A1* | 3/2016 | Mandl ..................... A61F 2/586 623/57 |
| 2020/0208689 A1* | 7/2020 | Sagmeister ............... A61F 2/64 |
| 2020/0360160 A1* | 11/2020 | Sagmeister ............... A61F 5/01 |

FOREIGN PATENT DOCUMENTS

| DE | 102012023173 A1 | 6/2014 |
| EP | 2836735 B1 | 2/2015 |

* cited by examiner

*Primary Examiner* — Bruce E Snow
(74) *Attorney, Agent, or Firm* — Holland & Hart LLP

(57) ABSTRACT

An orthopedic device with an end effector and a driving device, which is configured to drive the end effector by transferring a torque from the driving device to the end effector, wherein the orthopedic device features an overload protection that is configured to only prevent a transmission of a torque from the end effector to the driving device up to a threshold torque in at least one direction, and the overload protection includes at least a first coupling element and a second coupling element, which can be rotated relative to one another and which are coupled magnetically.

12 Claims, 6 Drawing Sheets

ORTHOPEDIC DEVICE

CROSS REFERENCE TO RELATED APPLICATIONS

This application is a U.S. National Entry and claims priority to PCT International Patent Application No. PCT/EP2018/070604, filed 30 Jul. 2018, and entitled "ORTHOPEDIC DEVICE", which claims priority to Germany Patent Application No. 10 2017 120 463.6 filed 6 Sep. 2017, the entire disclosures of which are incorporated herein by this reference.

TECHNICAL FIELD

The invention relates to an orthopedic device with an end effector and a driving device, which is configured to drive the end effector by transferring a torque from the driving device to the end effector.

BACKGROUND

This type of orthopedic device may be, for example, a prosthesis, especially a hand prosthesis, wherein in this case, the end effector is formed, for instance, of one or several fingers. Of course, other orthopedic devices, such as orthoses or other prostheses, are also conceivable, the end effector of which is designed differently.

In many configurations of this type of orthopedic device, it is practical to ensure that a position of the end effector, such as a position of a finger on a prosthetic hand, once reached, cannot or cannot immediately be altered by external influences, i.e. especially an external torque acting on the end effector. For example, if the user of such an orthopedic device grasps an object with a prosthetic hand, this object should not be able to be dropped. In the case of upper limb prostheses, for instance, the gripping, raising or rotating of end effectors is generally achieved by means of electric motors and corresponding gearboxes. In most of these cases, the force—such as a grip force—once applied, should also be maintained after switching off the current from the electric motor. However, this should be achieved without the current having to be maintained in order to save energy. Generally, this function is achieved by a lock, which blocks the drive train from being activated by external forces. By manipulating items which have been grasped, for example by raising them, considerably stronger external forces can act on the lock, which may cause the lock to become damaged. In this case, the lock must be protected. This can be achieved with the present invention. However, if the external torque becomes so great that components, such as the gearbox, the driving device or a lock, may become damaged, the end effector must be moved to prevent such damages from occurring. A damaged lock may mean, for instance, that an emergency opening of the effector, which can be provided for emergencies, can no longer be executed.

However, such external forces and/or torques, i.e. not generated by the driving device, that act on the end effector may be so great that they may cause the end effector to become damaged or destroyed, thereby causing considerable damage to the orthopedic device. Of course, this should be prevented, since the orthopedic device should be kept in good working order and the repair costs otherwise incurred avoided.

SUMMARY

The invention therefore aims to further develop an orthopedic device of the type de-scribed above to such an extent that a position and/or situation of the end effector, once reached, can be maintained while still safely preventing the end effector from becoming damaged.

The invention solves the problem by way of an orthopedic device according to the present disclosure, which includes an overload protection that is configured to only prevent a transmission of a torque from the end effector to the driving device up to a threshold torque in at least one direction, wherein the overload protection comprises at least one first coupling element and a second coupling element, which can be rotated relative to one another and which are coupled magnetically.

By way of such an overload protection, external torques are transferred to the preferably currentless driving device in such a way that the end effector can be moved at least in one direction by the external torque, so that the lock does not become damaged. Here, it may be quite sufficient to allow this movement, caused by external torques, in only one direction. For example, in the case of a closed prosthetic hand, a torque that is directed towards a further closing of the prosthetic hand is unproblematic. Only a torque acting in the opposite direction, which consequently aims to open the hand, cannot be transformed into such a movement, as long this cannot damage the lock. In other situations, for example if an opened prosthetic hand is moved towards an object to be grasped, a torque directed towards a further opening of the hand is unproblematic, whereas an external torque directed towards closing the hand, for instance because the wearer of the prosthetic hand strikes an object, such as a wall, with the hand, cannot lead to a corresponding movement unless the lock could otherwise be damaged.

In addition to protecting the driving device and the gearbox, such an overload protection protects the lock in particular, which prevents a transfer of the torque up to the threshold torque and, in a preferred configuration, forms part of the overload protection. The external torque acting on the end effector is absorbed by the lock. If it ex-ceeds the threshold torque, a decoupling takes place and it is no longer absorbed by the lock. This prevents the lock from becoming damaged.

Preferably, the overload protection prevents a transmission of the torque from the end effector to the driving device up to a threshold torque in both directions. This means that a torque that is smaller than the threshold torque and therefore cannot damage the lock or another component can be absorbed. A torque that is greater than the threshold torque may damage the lock or another component. Therefore, the overload protection causes a movement of the end effector to reduce the torque and protect the components from damage.

According to the invention, the overload protection comprises at least one first coupling element and a second coupling element, which are rotatably and magnetically coupled relative to one another.

The coupling elements are preferably arranged in such a way that a torque acting on the end effector is transmitted to the at least one first coupling element or the second coupling element. The two coupling elements are coupled magnetically, so that a force must be overcome to rotate the two coupling elements relative to one another. A torque is needed to achieve this. Provided that the external torque acting on the end effector does not exceed this threshold torque, the magnetic coupling between the coupling elements is so strong that a rotation, and therefore a movement of the end effector, does not occur. It is only upon exceeding this threshold torque that the force applied by way of the magnetic coupling is overcome, resulting in a movement of the coupling elements relative to one another. This ensures that a torque acting on the end effector, which is greater than the threshold torque, cannot damage any components.

The fact that a magnetic coupling is provided means that the overload protection can be designed to be physically small, which is particularly practical in the case of prosthetic hands, but also for many other orthopedic devices. Furthermore, the holding force, which is applied by the magnets and must be overcome by the torque, can be contactlessly transmitted, so that no friction effects occur and, in particular, no wear occurs as a result.

The second coupling element preferably features a multitude of magnets, preferably permanent magnets. The magnet holding force is generated by this multitude of magnets, which enables a more homogeneous distribution of the holding force, for instance, in the circumferential direction and also allows for the overload protection—and therefore also the orthopedic device in general—to be designed to be physically small. In a preferred configuration, the magnets are detachably arranged in specially provided indentations and/or recesses in the second coupling element. This ensures that the coupling forces exerted by the magnets and acting between the coupling elements can be adjusted individually and to meet the respective needs. This is especially easy to achieve by removing magnets from the corresponding indentations and/or recesses in order to reduce the magnetic holding forces or by placing additional magnets in the indentations and/or recesses so as to increase the magnetic holding forces. This renders it possible to adjust the threshold torque and in particular to select it such that any torques which are smaller than the set threshold torque cannot damage components such as the gearbox, the lock or the driving device.

It is especially preferable if the indentations and/or recesses are arranged to be equidistant across at least one section of the circumference, preferably across the entire circumference, of the second coupling element.

It has been proven beneficial for the orthopedic device to have two first coupling elements, between which the second coupling element is arranged. The forces generated by the magnets can thus be used on both sides of the magnets, in particular at their two pole ends. In a preferred embodiment, at least one of the coupling elements comprises a magnetizable material or is composed of such a material. This renders it possible to guide magnetic field lines into the material, which results in an especially high magnetic force. All first coupling elements are preferably designed to be identi-cal.

In a preferred configuration, at least one of the first coupling elements, preferably each of the first coupling elements, has a multitude of coupling regions, which are designed specifically in the form of tabs that protrude radially inwards, wherein preferably a quantity of the tabs corresponds to the number of the magnets and/or a number of the indentations and/or recesses. In this case, it is especially preferable if the first coupling elements are designed in the form of rings or ring-shaped discs, which feature the coupling regions. Of course, other coupling regions may be used, for example in the form of tabs that protrude radially outwards or in the form of elements made of material that can be magnetized particularly effectively. Specifically, if the number of tabs corresponds to the number of indentations and/or recesses, it ensures that—regardless of the number of magnets situated in the indentations and/or recesses—an effective a magnetic contact as possible is achieved between the various coupling elements. In such a case, if the threshold torque is exceeded due to an external torque acting on the end effector, the second coupling element moves relative to the first coupling elements in such a way that each of the magnets is moved away from the coupling region arranged closest to it and then allocated to the next coupling region following a predefined rotation. Here, the holding force applied by the magnets is again at a maximum, such that a further rotation of the coupling elements relative to one another is prevented as long as the external torque continues to not exceed the threshold torque.

In an especially preferable configuration, an additional raceway is arranged radially outside of the second coupling element, which is also preferably designed as a ring-shaped disc, said raceway being connected to the two first coupling elements, for example, such that it is torque-proof and thereby also connecting the two first coupling elements. Given that this ring is situated radially outside of the second coupling element, a closed circuit of lines of magnetic force is formed.

It is preferable for the at least one first coupling element or the second coupling element to be arranged on a housing such that it is torque-proof.

Preferably, the overload protection has a locking device that is configured to not af-fect the transfer of the torque from the driving device to the end effector and to prevent the transfer of the torque from the end effector to the driving device up to the threshold torque.

Such a locking device ensures that a movement of the end effector caused by the driving device occurs even with small and the smallest of torques, while external torques, which act on the end effector regardless of direction, do not cause a movement of the end effector as long as they do not exceed the threshold torque.

The locking device is preferably a jamming roller lock with a housing and a multitude of clamping discs, which are arranged in the housing such that they can be rotated and which each comprise at least one recess, in which a jamming roller is located, at least one driving projection and at least one driven projection, wherein the clamping discs are arranged and designed in such a way that a rotation of the clamping discs can be achieved by driving the driving projections and a rotation of the clamping discs can be prevented by driving the driven projections. The locking force can be almost arbitrarily scaled via the number of recesses and jamming rollers used. In addition to a jamming roller lock, all types of locks can be protected, such as a wrap spring lock.

BRIEF DESCRIPTION OF THE DRAWINGS

In the following, an example of an embodiment of the present invention will be ex-plained in more detail by way of the attached figures: They show.

DETAILED DESCRIPTION

Figure 1:
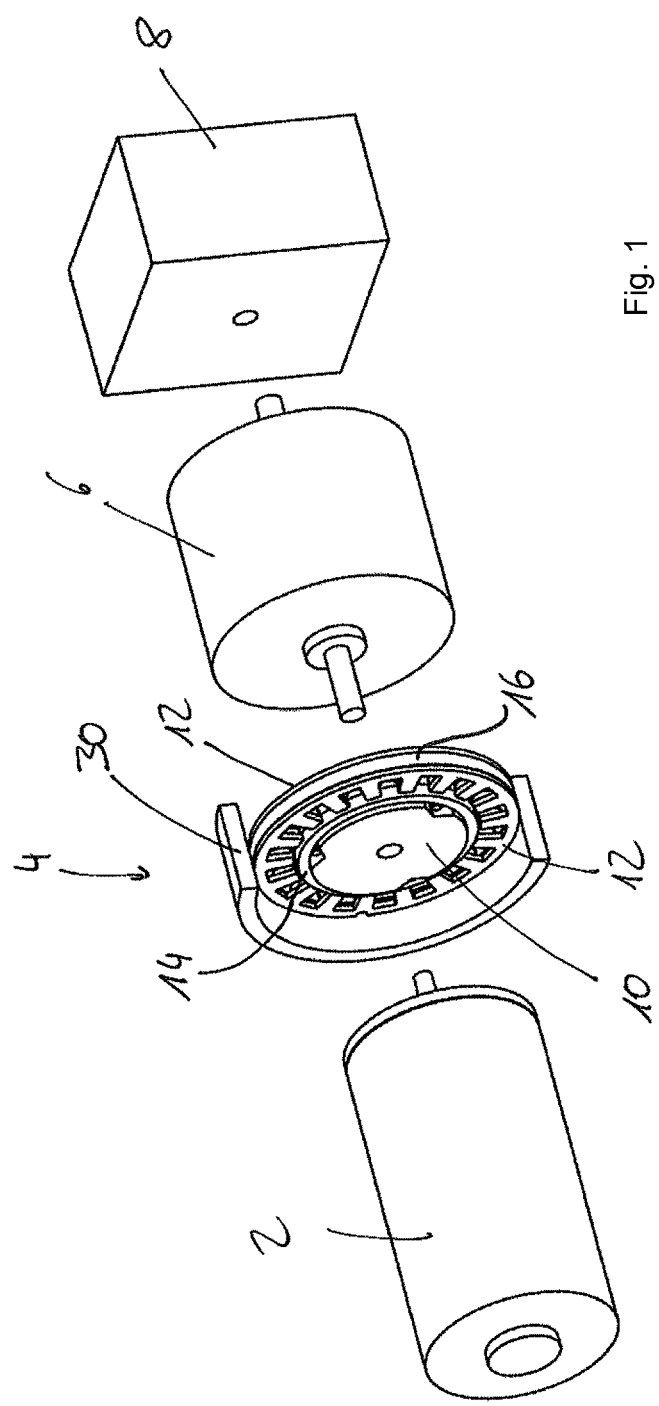
FIG. 1—a schematic depiction of a part of an orthopedic device according to a first example of an embodiment of the present invention, FIG. 2—the image from FIG. 1 with the overload protection in an exploded view, FIG. 3—a part of the overload protection from FIG. 2, FIG. 4—a sectional view through the components shown in FIG. 3, FIG. 5—an enlarged section from FIG. 4, FIG. 6—an axial top view of the components shown in FIG. 3, FIG. 7—an enlarged section from FIG. 6 and FIG. 8—an exploded view of a lock.

FIG. 1 shows a driving device 2, which may be designed, for instance, as an electric motor. It is coupled with an end effector 8 via an overload protection 4 and a gearbox 6, said end effector is only depicted schematically.

The overload protection 4 has a locking device 10, which is arranged inside the first coupling elements 12, between which a second coupling element 14 is arranged, and which are connected via a return ring 16. The return ring 16, the first coupling elements 12 and the second coupling element 14 are arranged in a housing 30.

Figure 2:
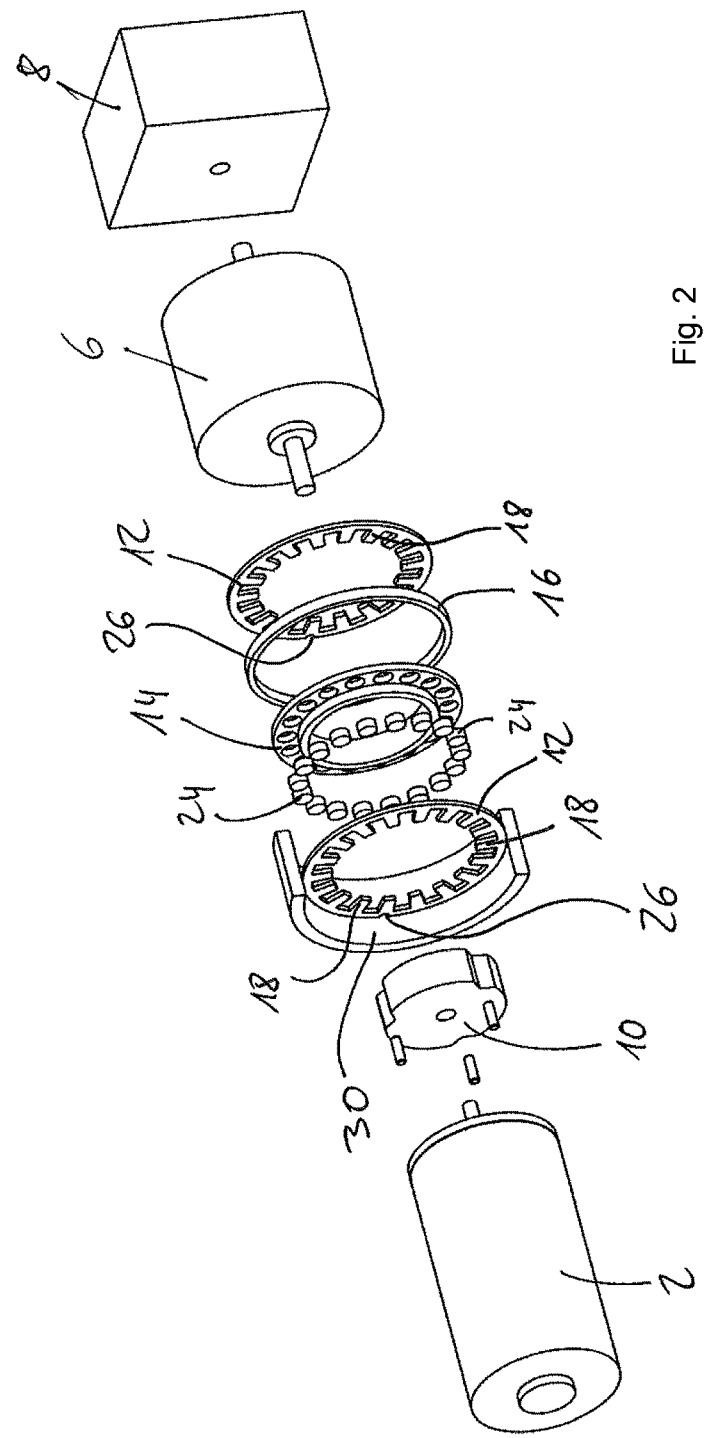

FIG. 2 shows the depiction from FIG. 1 with the driving device 2, the gearbox 6 and the end effector 8, wherein the overload protection 4 is shown in an exploded view.

The locking device 10 and various rings are visible, said rings being arranged in and next to one another. The first coupling elements 12 are designed as ring-shaped elements that feature a multitude of inward-protruding tabs 18, which act as coupling regions. A second coupling element 14 is situated between the two first coupling elements 12, wherein an inner side 20 of said second coupling element lies flat on the locking device 10 and said second coupling element features a multitude of recesses 22, into each of which a magnet 24 is inserted. The second coupling element 14 is surrounded by the return ring 16 which, when mounted, is connected with the first coupling elements 12 such that it is torque-proof. The first coupling elements 12 and the return ring 16 each feature a small groove 26 by way of which said coupling elements and the return ring can be arranged in a housing such that they are torque-proof.

Figure 3:
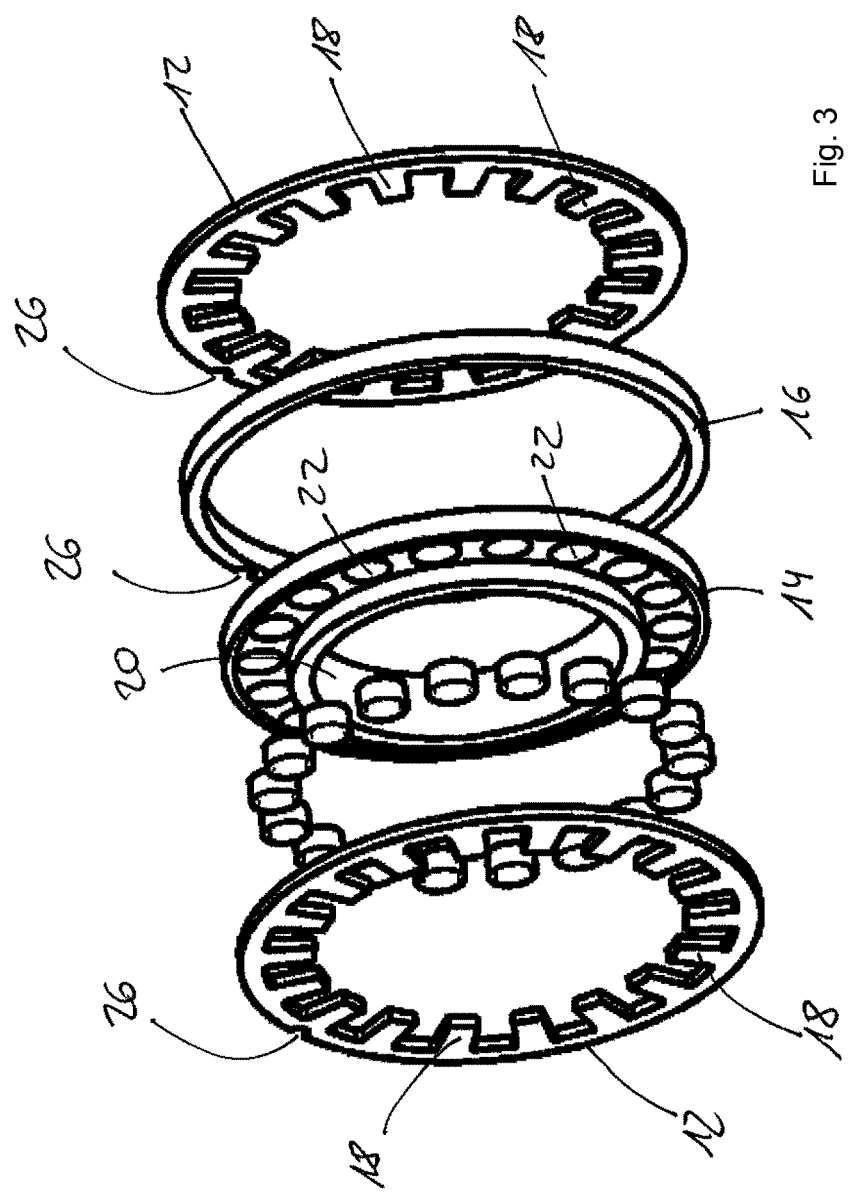

FIG. 3 depicts an exploded view of several parts of the overload protection 4. In particular, the groove 26 in the first coupling elements 12 and the return ring 16 are clearly visible. It is also clear to see that the inner side 20 of the second coupling element 14 is wider in the axial direction, i.e. from left to right in FIG. 3, than the part of the second coupling element 14 in which the recesses 22 are situated. This part of the second coupling element 14 also serves as a radial bearing for the two first cou-piing elements 12, the tabs 18 of which lie flat on this part of the second coupling element 14.

Figure 5:
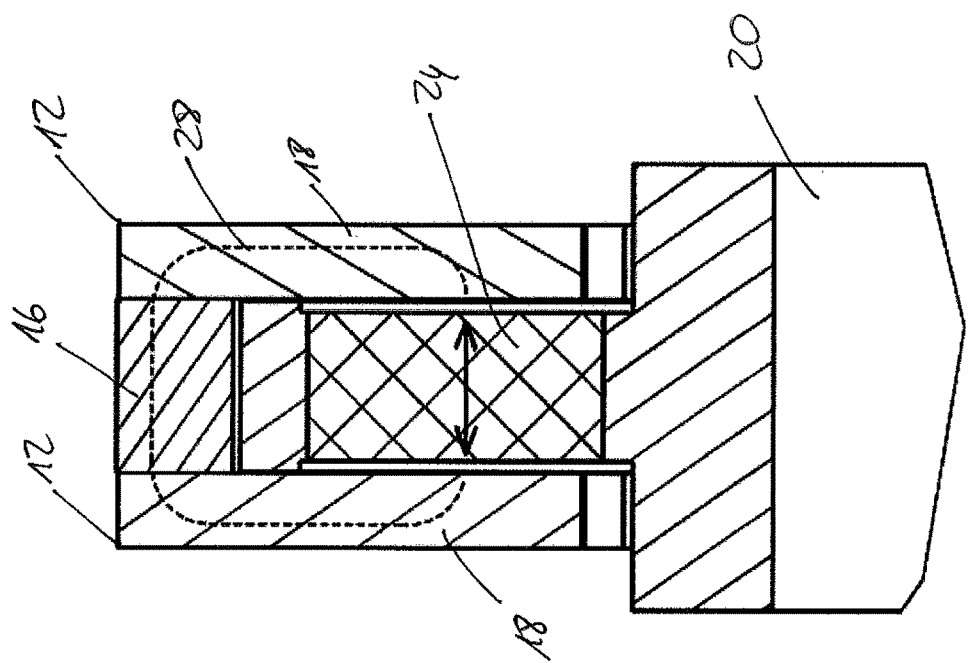
Figure 4:
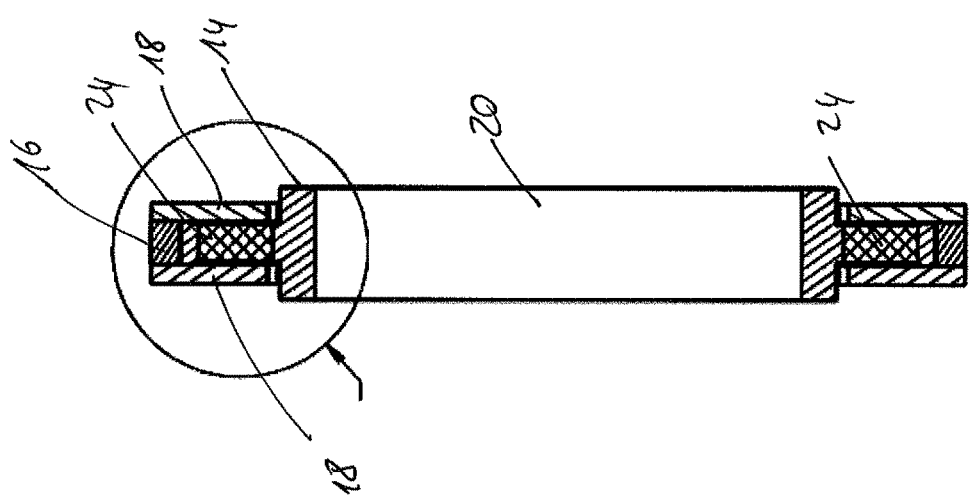

FIG. 4 shows a sectional view through the components shown in FIG. 3. The inner side 20 of the second coupling element 14 is wider than the remaining part of the second coupling element 14. The magnets 24 are surrounded by the respective tabs 18 and the return ring 16. This can be seen more clearly in FIG. 5, which depicts a section from FIG. 4. Clearly visible is one of the magnets 24, which is covered, in FIG. 5, on the right and the left by a tab 18 of one of the two first coupling elements 12. The two first coupling elements 12 are connected to one another radially outwards by the return ring 16. Given that at least the tabs 18, but preferably the com-plete first coupling elements 12 and especially preferably also the return ring 16, are made of a magnetizable material, the lines of force generated by the magnets 24 can be guided in the ring-shaped path 28, which is schematically depicted here.

Figure 7:
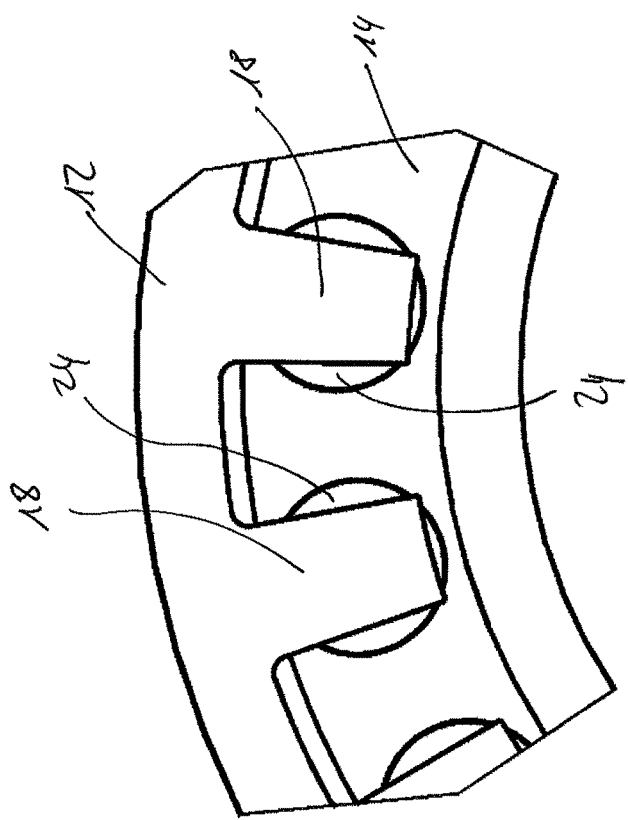
Figure 6:
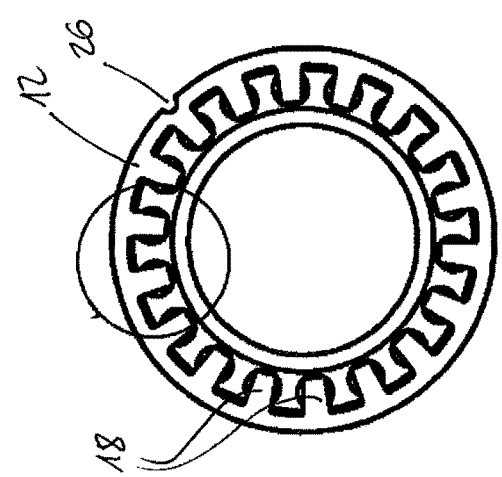

FIG. 6 depicts a schematic top view of one of the first coupling elements 12 with the groove 26 and the inward-protruding tabs 18. FIG. 7 shows an enlarged section: here, part of the first coupling element 12 with two tabs 18 and the magnets 24 situated underneath in the second coupling element 14 can be seen. If a torque acting on the end effector 8 is transferred by way of the locking device 10 to the second coupling element 14, a movement of the second coupling element 14 relative to the first coupling element 12 is initially prevented by the forces generated by the magnets 24 and the tabs 18 of the first coupling elements 12. The second coupling element 14 can only be moved relative to the first coupling elements 12 once a thus defined threshold torque is exceeded. To this end, the magnets 24 must be displaced relative to the tabs 18: a torque is required to achieve this. Following a displacement, which corresponds to the distance between two tabs 18, wherein said distance preferably also corresponds to the distance between the recesses in which the magnets 24 are situated, the situation—an enlargement of which is depicted in FIG. 7—occurs once again and the threshold torque must be overcome again.

Figure 8:
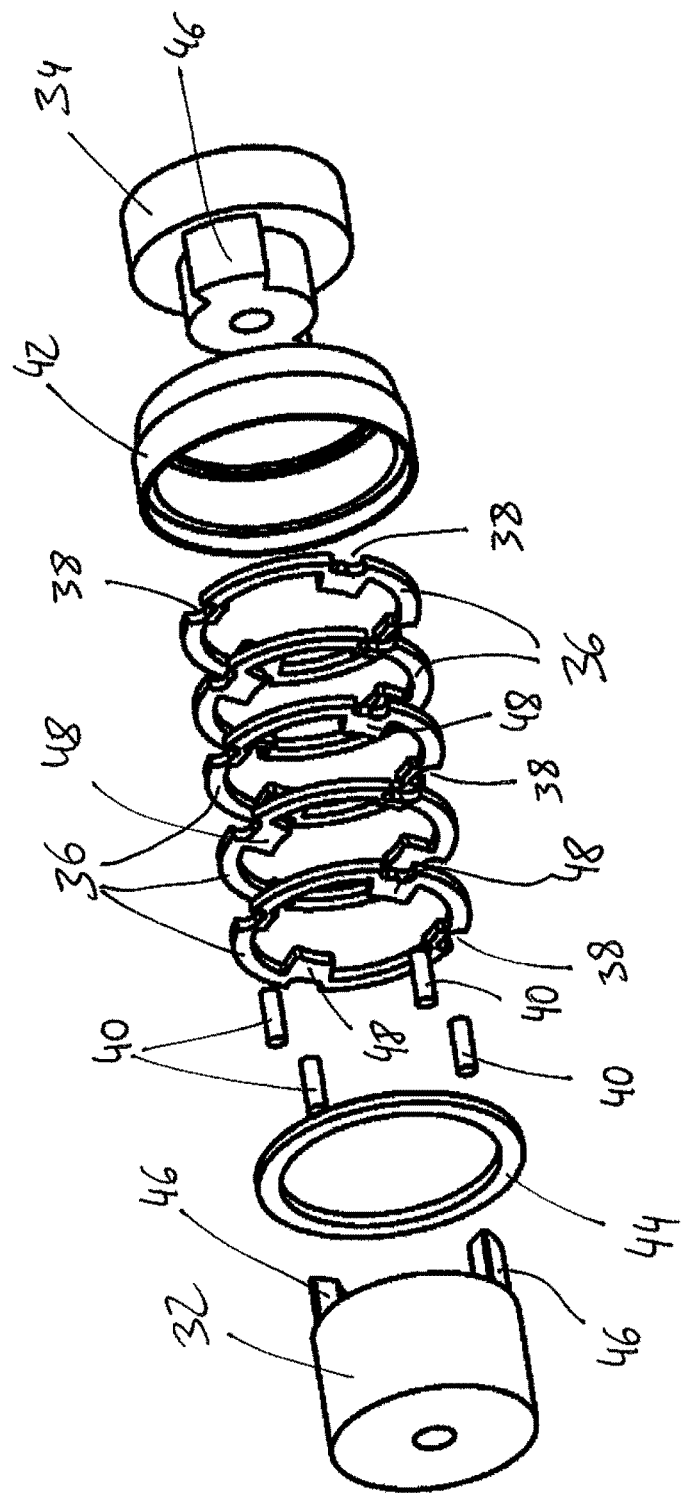

FIG. 8 depicts an exploded view of a jamming roller lock with a driver on the driving side 32 and a driver on the driven side 34. The jamming roller lock features five clamping discs 36, each of which has four recesses 38. Inside said recesses are four jamming rollers 40. The clamping discs 36 with the jamming rollers 40 are situated in a jamming roller housing 42, which restricts the recesses 38 radially outwards. In the example of an embodiment shown, a cover disc 44 prevents the jamming rollers 40 from being able to slip out of the recesses 38 in the axial direction.

Both the driver on the driving side 32 and the driver on the driven side 34 feature driver claws 46, with which they are or can be engaged with the driving projections or the driven projections.

In FIG. 8, it is clear that the clamping discs 36 are arranged at an offset to one another, such that an angle between the projections 48 of two adjacent clamping discs 36 in the example of an embodiment shown is 90°.

The invention claimed is:

1. An orthopedic device comprising:
an end effector;
a driving device which is configured to drive the end effector by transmitting a torque from the driving device to the end effector;
an overload protection that is configured to only prevent a transmission of a torque from the end effector to the driving device up to a threshold torque in at least one direction, the overload protection including at least one first coupling element and a second coupling element, which can be rotated relative to one another and which are coupled magnetically, wherein the second coupling element includes a plurality of magnets, and wherein the device has two first coupling elements, between which the second coupling element is arranged.

2. The orthopedic device according to claim 1, wherein the magnets are detachably arranged in at least one of specially provided indentations and specially provided recesses on the second coupling element.

3. The orthopedic device according to claim 2, wherein the at least one of indentations and recesses are arranged to be equidistant across at least one section of a circumference.

4. The orthopedic device according claim 1, wherein at least one of the first coupling elements has a plurality of coupling regions, which are designed in the form of tabs that protrude radially inwards, wherein a quantity of the tabs corresponds to at least one of the number of the magnets and a number of the at least one of indentations and recesses.

5. The orthopedic device according to claim 1, wherein at least one first coupling element or the second coupling element is arranged on a housing and is torque-proof.

6. The orthopedic device according to claim 1, wherein the overload protection has a locking device that is configured to not effect the transfer of the torque from the driving device to the end effector and to prevent the transfer of the torque from the end effector to the driving device up until the point of the threshold torque.

7. An orthopedic device comprising:
an end effector;
a driving device configured to transmit a torque to drive the end effector;
an overload protection configured to prevent a transmission of a torque from the end effector to the driving device up to a threshold torque in at least one direction, the overload protection including at least one first coupling element and a second coupling element, the first and second coupling elements being rotatable relative to each other and being coupled magnetically, wherein the second coupling element includes a plurality of magnets, and wherein the device has two first coupling elements, the second coupling element being arranged between the first coupling elements.

8. The orthopedic device according to claim 7, wherein the magnets are detachably arranged in at least one of specially provided indentations and specially provided recesses on the second coupling element.

9. The orthopedic device according to claim 8, wherein the indentations and recesses are equidistant across at least one section of a circumference.

10. The orthopedic device according claim 7, wherein at least one of the first coupling elements has a plurality of coupling regions, which are designed in the form of tabs that protrude radially inwards, and the tabs correspond to at least one of the number of the magnets and a number of the indentations or recesses.

11. The orthopedic device according to claim 7, wherein the at least one first coupling element or the second coupling element is arranged on a housing and is torque-proof.

12. The orthopedic device according to claim 7, wherein the overload protection has a locking device that is configured to avoid transfer of the torque from the driving device to the end effector and to prevent the transfer of the torque from the end effector to the driving device up to the threshold torque.

* * * * *